United States Patent [19]

Baker

[11] Patent Number: 4,955,666
[45] Date of Patent: Sep. 11, 1990

[54] SURGICAL CHAIR OR TABLE WITH DEBRIS-CATCHING FACILITY AND DISPOSABLE CATCH BAG THEREFOR

[75] Inventor: Jeffrey H. Baker, Sandy, Utah

[73] Assignee: M-D, Inc., West Valley City, Utah

[21] Appl. No.: 355,230

[22] Filed: May 19, 1989

Related U.S. Application Data

[63] Continuation-in-part of Ser. No. 332,333, Apr. 3, 1989, abandoned.

[51] Int. Cl.$^5$ ............................................. A47D 15/00
[52] U.S. Cl. ..................................... 297/182; 108/26; 5/485; 297/219
[58] Field of Search ..................... 297/182, 219; 5/485, 5/503; 108/26

[56] References Cited

U.S. PATENT DOCUMENTS

| | | | |
|---|---|---|---|
| 439,088 | 10/1890 | Allen | 297/357 X |
| 837,570 | 12/1906 | Jackson | 297/182 |
| 849,974 | 4/1907 | Cantrell | 108/26 |
| 1,050,205 | 1/1913 | Conley | 297/182 |
| 1,425,952 | 8/1922 | Fidler | 5/485 |
| 2,938,574 | 5/1960 | Brown | 297/182 |
| 3,697,127 | 10/1972 | Robertson | 297/182 |

Primary Examiner—Laurie K. Cranmer
Attorney, Agent, or Firm—Mallinckrodt & Mallinckrodt

[57] ABSTRACT

A chair or table for medical or surgical patients has in one form of the invention an outwardly bowed facility, preferably removable and replaceable, along an end of the chair or table down whose seat or top liquid and debris cascades during an examination or surgical procedure, to receive and retain a flap extending from and along one margin of the opening of a catch bag of flexible sheet material while a second flap, extending from and along the opposite margin of such opening of the catch bag, overlies the seat of the chair or the table top at such end of the chair or table and is preferably secured to such chair seat or table top by pressure sensitive adhesive applied to the overlying flap of the bag. In another form of the invention, the catch receptacle itself has an elongate stiff but malleable member incorporated therein extending along such opposite margin of the bag opening for bending outwardly of the opening to hold the bag open when installed on the chair or table.

20 Claims, 2 Drawing Sheets

SURGICAL CHAIR OR TABLE WITH DEBRIS-CATCHING FACILITY AND DISPOSABLE CATCH BAG THEREFOR

PRIOR APPLICATION

This application is a continuation-in-part of my presently pending, similarly entitled, application Ser. No. 07/332,333, filed Apr. 3, 1989 now abandoned.

BACKGROUND OF THE INVENTION

1. Field: The invention is in the field of medical and surgical examination or operative chairs or tables equipped to catch liquids and debris resulting from examining, or from operating upon, a patient. It is also concerned with disposable bags capable of use as catch receptacles for such chairs or tables.

2. State of the Art: Surgical operative chairs for use by gynocologists in carrying out various examination and surgical procedures on their patients are normally equipped with catch receptacles forwardly of the chair seat so as to receive liquid and debris resulting from the examination or surgical procedure as it flows by gravity along the chair seat. The catch receptacle is ordinarily a rigid vessel, e.g. a drawer recessed in the front of the seat for being partially pulled out during an examination or surgical procedure to receive liquid and debris cascading over the forward portion of the seating surface. Following such examination or surgical procedure, the drawer is removed entirely for emptying and washing.

SUMMARY OF THE INVENTION

A principal object in the making of the invention was to provide a disposable bag to serve as the catch receptacle and to equip a medical examination or surgical chair or table with facilities for temporarily holding such bag in catch position.

A further object was to construct and hold the bag in such a way as to protectively cover critical portions of the chair seat or table top as well as to catch the liquid or debris cascading over the protectively covered part of the chair seat or table top.

In accomplishing these objectives of the invention, one embodiment of the invention includes a bag of flexible, liquid impervious, sheet material, such as any one of a number of widely used plastic bag materials, fabricated with front and back panels and with relatively narrow side panels that define a relatively wide from side-to-side, and narrow from front-to-back, bag opening therebetween. The bottom of the bag is closed, and elongate flaps extend from front panel and back panel, respectively, at and along the bag opening, whereby the front flap can be hung over a retention bar attached to and spaced forwardly from the front of the chair seat or table top, and the back flap can be spread protectively over the forward portion of the chair seat or table top to be sat or laid on and thus held in place by a patient occupying the chair or table.

For this purpose, the front of the chair seat or table top is provided with a bag-retention bar spaced somewhat forwardly of such chair seat or table top to accommodate the bag therebetween, such bar being preferably of bow or generally similar shape with opposite ends that can be plugged into receiving facilities provided at opposite sides of the front of the chair seat or table top, and the back flap of the bag preferably having a pressure sensitive adhesive applied to its back surface for temporary adhesion to the chair seat or table top or to any other protective covering that may have been previously applied thereto.

In other embodiments of the invention, sheets of plastic material are placed face-to-face and heat sealed along opposite side margins for a distance that leaves separate front and rear flaps and no side panels. In a presently preferred form, the retention bar is incorporated as one or more stiff but malleable wires in the bags as fabricated. The wire is bent outwardly by the user and holds the bag open without being attached to the chair.

THE DRAWINGS

The best modes presently contemplated for carrying out the invention in actual practice are illustrated in the accompanying drawings in which:

FIG. 1 is a pictorial view, looking from the front of a gynocologists examination or surgical operating chair equipped for and, as shown, holding a vaginal debris bag in accordance with the invention;

FIG. 2, a pictorial view of the vaginal debris bag of FIG. 1 drawn to a considerably larger scale and showing the back flap in an artifically raised position, with a strip of pressure sensitive adhesive applied across the back face thereof as indicated by broken lines;

FIG. 3, a fragmentary vertical section taken along the line 3—3 of FIG. 1 and drawn to approximately the same scale as that of FIG. 2;

FIG. 4, a fragmentary horizontal section taken on the line 4—4 of FIG. 3;

FIG. 5, a view corresponding to that of FIG. 2, but showing a somewhat different embodiment of bag;

FIG. 6, a view corresponding to that of FIG. 3, but showing the embodiment of FIG. 5;

FIG. 7, a pictorial view of the bag of FIGS. 1 and 2 with flaps tied together to close the bag for disposal; and FIG. 8, a view corresponding to that of FIG. 2 but drawn to a reduced scale and showing a different embodiment in which side panels are eliminated and the retention member is a stiff but malleable wire tape incorporated in the bag as fabricated.

DETAILED DESCRIPTION OF THE ILLUSTRATED EMBODIMENTS

Figure 1:
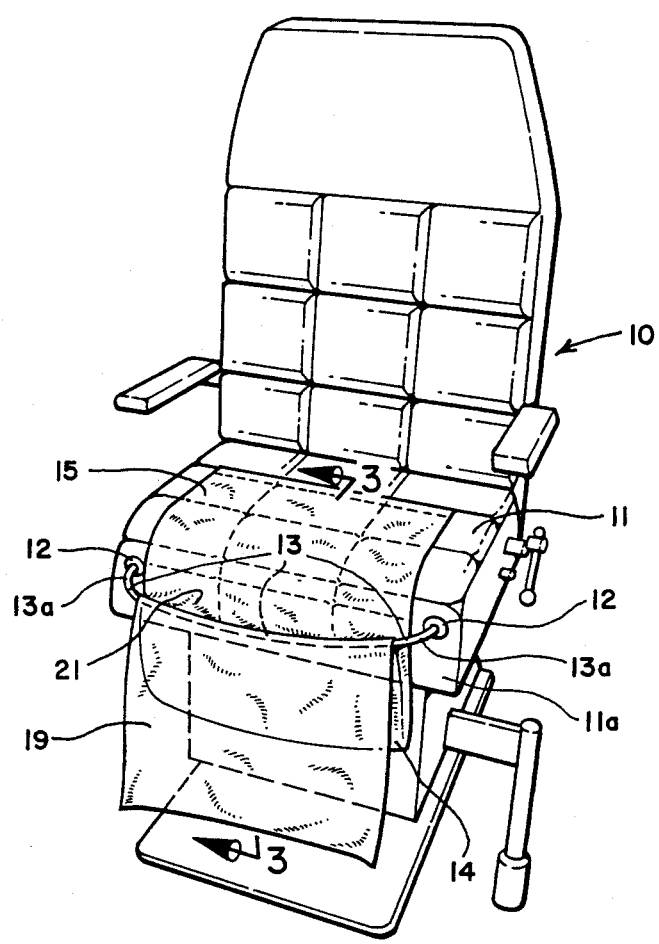
Figure 2:
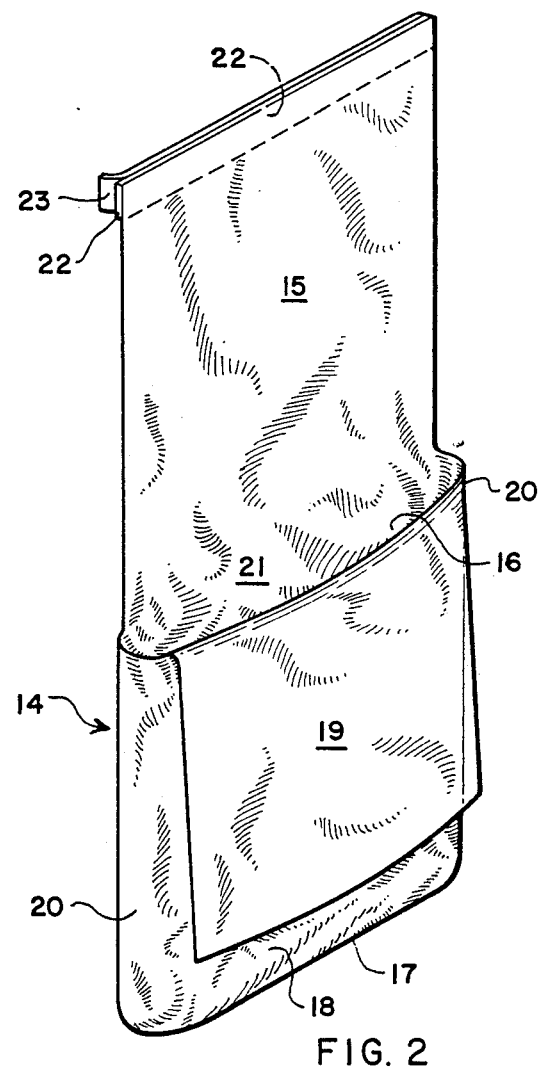

As illustrated, the chair 10 of FIG. 1 is typical of those used by gynocologists for vaginal surgery and contains nothing new except provision at the front 11a of the chair seat 11 of plug-in fittings 12 at opposite sides, respectively, of such chair seat front 11a for receiving opposite ends 13a, respectively, of a bowed, rigid, bag-retention rod 13.

Figure 3:
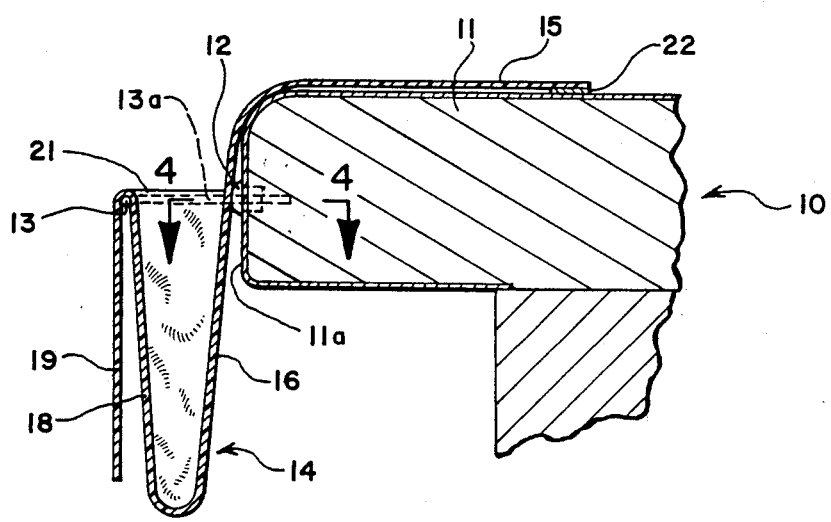
Figure 4:
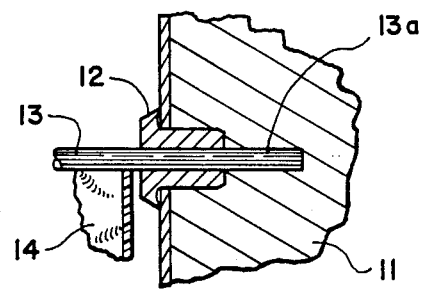

A disposable, vaginal-debris-receiving-and-retaining bag 14 of flexible, liquid impervious, sheet material, usually a sheet plastic customarily used in the fabrication of bags for a variety of purposes, is hung in the space between chair seat front 11a and rod 13 as shown in FIG. 3.

Bags 14 may be fabricated sequentially from an elongate tube of the plastic material by cutting such tube transversely into lengths sufficiently long to provide for a flap 15 extending from the bag back panel 16 to protectively cover a desired extent of the forward portion of the chair seat 11, as indicated in FIGS. 1 and 3. Such tube is then heat sealed in usual manner transversely at one end to provide a closed bottom 17 between a back panel 16 and a front panel 18, and the sides of the tube are cut out from the opposite, open end to form a back flap 15 and a front flap 19, leaving the bag proper 14 with side panels 20, respectively, between back panel 16 and front panel 18, which panels define a receiving opening 21 for the bag.

In installing a bag 14 as a catch receptacle, front flap 19 is hung over retention rod 13 as shown in FIGS. 1 and 3, and back flap 15 is turned backwardly to cover the forward portion of chair seat 11.

It is preferred that the surface of the back face of back flap 15 have applied thereto means for adhering to chair seat 11 or to a pre-applied cover therefor under the weight of a patient sitting in the chair, e.g. a strip 22 or patches of a pressure-sensitive adhesive, covered in conventional manner by a removable protective strip 23.

During the surgery, liquid and other surgical debris will cascade down the front of the chair seat over protective flap 15 of the bag and will be caught by the bag. It should be noted that, contrary to rigid catch receptacles customarily employed for the purpose, the holding capacity of the bag will not be lessened if the chair seat is titled during the operative procedure but will hang freely to accommodate the tilt.

The relatively narrow receiving opening 21 of bag 14 preferably has overall width that approximates the width of the front of the chair seat minus a few inches on each side, so as to catch all of the cascading liquid or debris. Back flap 15 extends from and along the back width margin of reveiving opening 21 to protectively cover the desired extent of the forward portion of chair seat 11.

If a table is used instead of a chair, the bag 14 is similarly positioned as a catch receptacle and the retention rod 13 is the same.

Figure 5:
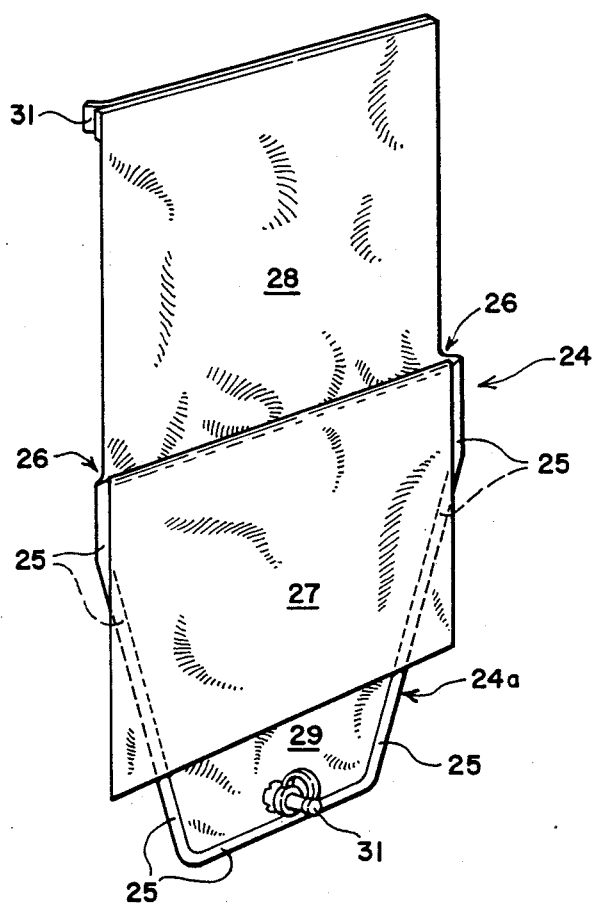

The bags may be fabricated in any way found best by given supplier to fit any given need. Thus, instead of the bags having side panels 20, as in the bag 14, bags 24, FIGS. 5 and 6, may be fabricated by placing two sheets of flexible plastic face-to-face and heat sealing along side and bottom margins, as at 25. Then, upper portions of the heat-sealed margins at opposite sides of the sheets, respectively, are cut away, as at 26, along a sufficient length from the upper ends of the sheets to form front and rear flaps 27 and 28, respectively, extending upwardly from front and rear panels 29 and 30, respectively.

The bag 24 in the illustrated instances is intended for use during urological surgery. The edges of its opposite sides converge along the lower portion of the bag to provide a narrower bag portion 24a leading to a discharge spigot 31 or hose barb sealingly affixed in, and near the bottom of, the front panel 29 of the bag for draining the bag into a manually-carried vessel which may be emptied at intervals as required.

Such bag 24, with or without the convergent lower portion 24a or the spigot 31, may be used as is bag 14 with a chair 10 and bag-retention rod 13 for any purpose, a protectively covered, pressure sensitive adhesive, attachment strip 31 being provided, as in bag 14, if desired, for temporary adhesion to the chair seat or table top during use of the bag.

Figure 6:
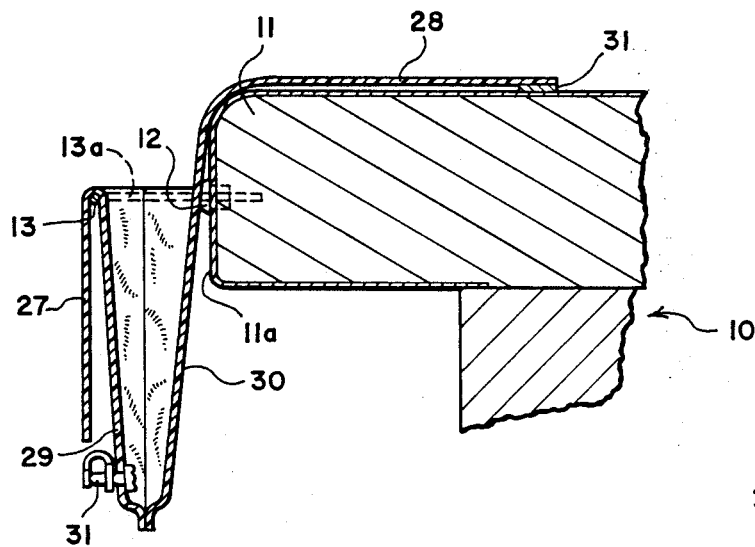

However fabricated to provide a debris-retaining bag portion and upper front and rear flaps, the flaps may be made long engough to provide for closing of the debris-containing bag after its removal from the chair or table by tying such flaps together, as in FIG. 6, thereby helping to retain the contents and to prevent spilling while carrying the bag to a location of disposal.

Figure 7:
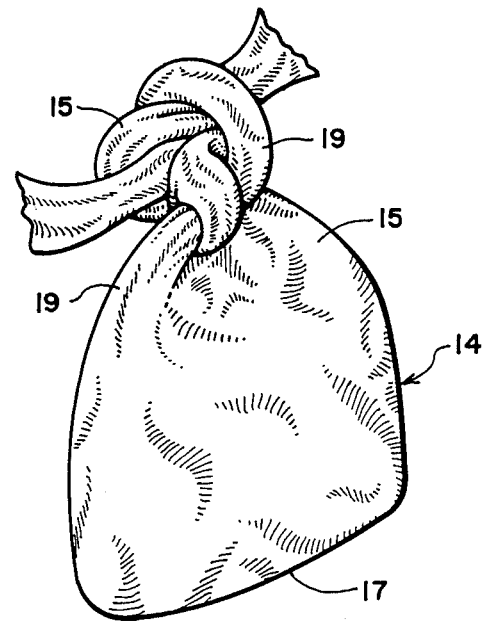
Figure 8:
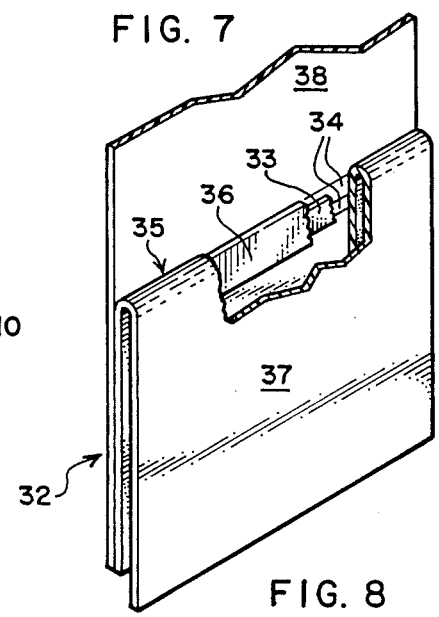

A presently preferred embodiment is to fabricate the bag 32, FIG. 8, as is bag 24 from face-to-face sheets of plastic, although as here shown the bag is shaped as is bag 14, and to include an elongate, stiff but malleable member 33 as a substitute for the retention rod 13 of the previously described embodiments which plugs into the front of chair 10. Such malleable member 33 is preferably a prefabricated tape having a pair of elongate stiff but malleable wires 34, respectively, of malleable metal heat sealed along opposite longitudinal margins of a flexible plastic tape body. Such tape is laid flat on the outside face of the front panel of the bag proper bordering the bag opening 35 and is covered by a strip of wider adherent tape 36 to hold it in place. Member 33 can be easily bent but will hold its shape after bending. Although the bag need not have a front flap corresponding to those front flaps 19 and 27 of the previously described embodiments, it preferably does have such a front flap 37 for tying to the back flap 38 in the manner shown in FIG. 7. Back flaps 38 serves the same purpose in the use of the bag with a chair or table as do the back panels 16 and 30 of the previously described embodiments.

For use with a chair or table, the elongate malleable retention member 33 is merely bent outwardly of bag opening 35 to bowed shape so as to hold the bag open when it is hung in front of the chair, with the opposite ends of such member confronting but not necessarily abutting against the front of the chair seat or table top.

Thus, in accordance with the invention the bag has a flap extending upwardly from its rear panel along the width margin of the bag opening for overlying a chair seat or table top with the bag proper hanging therefrom in front of the chair seat or table top and has means extending along the other width margin of the bag opening for bowing outwardly of the opening in the forming of the opening to receive the liquid and debris from the chair seat or table top. Such means may be a second flap extending upwardly from the front panel along the margins of the opening for hanging over a rigid bar bowed outwardly of the chair seat or table top and whose opposite ends are attached to the chair seat or table top, or it may be an elongate malleable member attached to the bag itself for being bowed outwardly of the opening when the bag is being prepared for use with a chair or table, a front flap being preferably but not necessarily present.

Whereas this invention is here illustrated and described with specific reference to embodiments thereof presently contemplated as the best modes of carrying out such invention in actual practice, it is to be understood that various changes may be made in adapting the invention to different embodiments without departing from the broader inventive concepts disclosed herein and comprehended by the claims that follow.

I claim:

1. A disposable receptacle for use with a medical or surgical chair or table during examination of, or a surgical procedure on, a patient sitting or lying on the chair or table so as to protect the chair or table from soiling or contamination by liquids and debris used in or resulting from the examination or surgical procedure and to collect and retain such liquids and debris for disposal, comprising a wide bag of disposable, liquid-impervious, flexible sheet material having a relatively narrow receiving opening extending from side-to-side of the bag;

a flap of similar sheet material extending from and along one width margins of said opening for covering an adjacent portion of the seat of the chair or the top of the table that is likely to be soiled during said examination or surgical procedure when said bag is positioned at the front of said chair or table in open condition at or below the level of said seat of the chair or top of the table to be held in place under the weight of a patient sitting or lying on said flap; and means extending along another width margin of said opening for bowing outwardly of said opening in the forming of said opening to receive said liquids and debris.

2. A disposable receptacle according to claim 1, wherein the means for bowing outwardly is a flap of similar sheet material adapted to hang over an outwardly bowed support attached to and spaced from the chair or table.

3. A disposable receptacle according to claim 2, wherein the sheet material of the flaps is integral with the sheet material of the bag.

4. A disposable receptacle according to claim 2, wherein the bag has front and rear panels and relatively narrow side panels, and the flaps are upward extensions of the front and rear panels, respectively, along widths thereof at the margins of the receiving opening of the bag.

5. A disposable receptacle according to claim 2, wherein the bag has front and rear panels formed by respective sheets of the flexible sheet material placed in face-to-face contiguous relationship, said sheets being secured together by sealing their margins together along the bottom and sides of the bag but not along the top of the bag, the sealed side margins terminating at the unsealed and open top of the bag, and the flaps extending upwardly from the front and rear panels of the bag along the width thereof at the margins of the receiving opening of the bag.

6. A disposable receptacle according to claim 2, including means on the surface of one of the flaps that faces outwardly away from the opening of the bag for adhering to the seat of the chair or the top of the table or to a cover thereover under the weight of a patient sitting or lying thereon.

7. A disposable receptacle according to claim 6, wherein the adhering means comprises pressure-sensitive adhesive applied to the surface of the flaps.

8. A disposable receptable according to claim 1, wherein the means for bowing outwardly in an elongate stiff but malleable member attached to the bag.

9. A disposable receptacle according to claim 8, wherein the elongate malleable member is a length of flexible tape incorporating at least one stiff but malleable wire extending longitudinally therethrough.

10. A disposable receptacle according to claim 9, wherein the length of flexible tape is secured to a face of the bag along the opening by means of a wider overlying flexible tape overlying said first-named length of flexible tape.

11. A medical or surgical chair or table having a normally substantially horizontal, patient-receiving surface and a depending surface at one end of said patient-receiving surface at which a bag for receiving liquids and debris from a patient occupying the chair or table can be positioned; a substantially rigid, elongate supporting member for such a bag, said member having an elongate portion intermediate its opposite ends that is adapted to be spaced from said depending surface when said supporting member is attached to said chair or table at said depending surface thereof for supporting said bag is open receiving condition; and means at opposite lateral sides of said depending surface for removably attaching opposite ends of said supporting member to said chair or table so as to receive and hold such a bag in open receiving position and condition.

12. A medical or surgical chair or table according to claim 11, wherein the bag supporting member is a rod.

13. A medical or surgical chair or table according to claim 12, wherein the means for holding the bag-supporting rod are a pair of openings through the depending surface of the chair or table at respectively opposite lateral sides of the chair or table for receiving and removably retaining opposite end portions of said bag-supporting rod.

14. A medical examination chair or table according to claim 11, wherein the bag-supporting member is attached to the chair or table in bag-supporting position; and a disposable bag of liquid impervious, flexible sheet material is removably attached to said chair or table and to said supporting member, said bag having a relatively narrow receiving opening extending from side-to-side of the bag; a flap of similar sheet material extending from and along one of the width margins of said opening for covering an adjacent portion of the seat of the chair or the top of the table that is likely to be soiled during said examination or surgical procedure when said bag is attached to the front of said chair or table in open condition at or below the level of said seat of the chair or top of the table to be held in place under the weight of a patient sitting or lying thereon; and a flap of similar sheet material extending from and along the other width margin of said opening for hanging over a support attached to and spaced from said chair or table.

15. A disposable receptacle for attachment to a medical or surgical chair or table during examination of, or a surgical procedure on, a patient sitting or lying on the chair or table so as to protect the chair or table from soiling or contamination by liquids and debris used in a resulting from the examination or surgical procedure and to collect and retain such liquids and debris for disposal, comprising a wide bag of disposable, liquid-impervious, flexible sheet material having a relatively narrow receiving opening extending from side-to-side of the bag; a flap of similar sheet material extending from and along one of the width margins of said opening for covering an adjacent portion of the seat of the chair or the top of the table that is likely to be soiled during said examination or surgical procedure when said bag is attached to the front of said chair or table in open condition at or below the level of said seal of the chair or top of the table to be held in place under the weight of a patient sitting or lying thereon; and a flap of similar sheet material extending from and along the other width margin of said opening for hanging over a support attached to and spaced from said chair or table.

16. A disposable receptacle according to claim 15, wherein the sheet material of the flaps is integral with the sheet material of the bag.

17. A disposable receptacle according to claim 15, wherein the bag has front and rear panels and relatively narrow side panels, and the flaps are upward extensions of the front and rear panels, respectively, along the widths thereof at the margins of the receiving opening of the bag.

18. A disposable receptacle according to claim 15, wherein the bag has front and rear panels formed by respective sheets of the flexible sheet material placed in face-to-face contiguous relationship, said sheets being secured together by sealing their margins together along the bottom and sides of the bag but not along the top of the bag, the sealed side margins terminating at the unsealed and open top of the bag, and the flaps extending upwardly from the front and rear panels of the bag along the width thereof at the margins of the receiving opening of the bag.

19. A disposable receptacle according to claim 15, including means on the surface of one of the flaps that faces outwardly away from the opening of the bag for adhering to the seat of the chair or the top of the table or to a cover thereover under the weight of a patient sitting or lying thereon.

20. A disposable receptacle according to claim 19, wherein the adhering means comprises pressure-sensitive adhesive applied to the surface of the flaps.

* * * * *

UNITED STATES PATENT AND TRADEMARK OFFICE
CERTIFICATE OF CORRECTION

PATENT NO. : 4,955,666

DATED : September 11, 1990

INVENTOR(S) : Jeffrey H. Baker

It is certified that error appears in the above-identified patent and that said Letters Patent is hereby corrected as shown below:

Column 3, line 31, "reveiving" should be "receiving", line 37, insert "any" after "found best by", line 66, "engough" should be "enough".

Signed and Sealed this

Twenty-eighth Day of January, 1992

Attest:

HARRY F. MANBECK, JR.

*Attesting Officer*      *Commissioner of Patents and Trademarks*